United States Patent
Gengyo et al.

(10) Patent No.: US 10,500,774 B2
(45) Date of Patent: Dec. 10, 2019

(54) METHOD FOR MANUFACTURING INTERDENTAL CLEANING DEVICE

(71) Applicant: SUNSTAR SUISSE S.A., Etoy (CH)

(72) Inventors: Anri Gengyo, Takatsuki (JP); Keisuke Kato, Takatsuki (JP); Jurgen Butz, Schonau (DE)

(73) Assignee: SUNSTAR SUISSE S.A., Etoy (CH)

(*) Notice: Subject to any disclaimer, the term of this patent is extended or adjusted under 35 U.S.C. 154(b) by 231 days.

(21) Appl. No.: 15/525,171

(22) PCT Filed: Nov. 11, 2015

(86) PCT No.: PCT/JP2015/081789
§ 371 (c)(1),
(2) Date: May 8, 2017

(87) PCT Pub. No.: WO2016/076373
PCT Pub. Date: May 19, 2016

(65) Prior Publication Data
US 2017/0319310 A1 Nov. 9, 2017

(30) Foreign Application Priority Data
Nov. 11, 2014 (JP) .................. 2014-229296

(51) Int. Cl.
*B29C 45/14* (2006.01)
*B29C 45/26* (2006.01)
(Continued)

(52) U.S. Cl.
CPC .... *B29C 45/14622* (2013.01); *A46B 15/0093* (2013.01); *A46D 3/00* (2013.01);
(Continued)

(58) Field of Classification Search
CPC ............ B29C 45/14622; B29C 45/125; B29C 45/2735
See application file for complete search history.

(56) References Cited

U.S. PATENT DOCUMENTS 3,659,997 A * 5/1972 Rees .................... B29C 45/125
425/575
4,212,624 A * 7/1980 Ando .................... B29C 45/27
425/548

(Continued)

FOREIGN PATENT DOCUMENTS

JP       3002668 B1    1/2000
JP    2001-506514 A1    5/2001
(Continued)

OTHER PUBLICATIONS

Rees, Herbert. Mold engineering. Hanser Verlag, Jun. 15, 2002. (Year: 2002).*

(Continued)

*Primary Examiner* — Benjamin A Schiffman
(74) *Attorney, Agent, or Firm* — Kratz, Quitos & Hanson, LLP

(57) ABSTRACT

Provided is a method for manufacturing an interdental cleaning device (1) including a base portion (10) having a handle portion (11) and a core portion (12); and a soft portion (20) having a cleaning soft portion (21), a non-slip portion (22), and connecting portions (23) extending from two sites of the non-slip portion (22) and being connected to the cleaning soft portion (21). The method includes causing a second gate (49) of second molds (40) and (41) for molding the soft portion (20) to open at a position substantially equally distant from positions of two communicating openings (48*a*) of a non-slip molding space (47) for molding the non-slip portion (22), the two communicating openings (48*a*) communicating with connecting portion molding (Continued)

spaces (48) for molding the connecting portions (23); and charging the elastomeric material from the second gate (49) into a second molding space (42) for molding the soft portion (20) to fill the molding space (42).

6 Claims, 13 Drawing Sheets

(51) Int. Cl.
  *A61C 15/02* (2006.01)
  *A46B 15/00* (2006.01)
  *A46D 3/00* (2006.01)
  *B29C 45/12* (2006.01)
  *B29C 45/27* (2006.01)
  *B29C 45/16* (2006.01)
  *B29K 21/00* (2006.01)
  *B29L 31/42* (2006.01)

(52) U.S. Cl.
  CPC ............ *A61C 15/02* (2013.01); *B29C 45/125* (2013.01); *B29C 45/14336* (2013.01); *B29C 45/1676* (2013.01); *B29C 45/2626* (2013.01); *B29C 45/2735* (2013.01); *A46B 2200/108* (2013.01); *B29K 2021/006* (2013.01); *B29L 2031/425* (2013.01)

(56) References Cited

U.S. PATENT DOCUMENTS

| | | | | |
|---|---|---|---|---|
| 4,260,359 A | * | 4/1981 | Dannels | ................ B29C 45/125 |
| | | | | 425/543 |
| 4,290,744 A | * | 9/1981 | Dannels | ................ B29C 45/561 |
| | | | | 264/328.7 |
| 2006/0233911 A1 | * | 10/2006 | Spuller | ............... B29C 45/2735 |
| | | | | 425/564 |
| 2007/0212444 A1 | * | 9/2007 | Fairy | ....................... B29C 45/27 |
| | | | | 425/564 |
| 2009/0230756 A1 | * | 9/2009 | Crossman | ................ A46B 5/02 |
| | | | | 300/21 |
| 2015/0114428 A1 | * | 4/2015 | Kato | .................. A46B 15/0093 |
| | | | | 132/329 |

FOREIGN PATENT DOCUMENTS

| | | |
|---|---|---|
| JP | 4236571 B2 | 3/2009 |
| JP | 2012-71449 A1 | 4/2012 |
| JP | 2013-188299 A1 | 9/2013 |
| WO | 2013/176297 A1 | 11/2013 |
| WO | 2014/005659 A1 | 1/2014 |

OTHER PUBLICATIONS

Machine translation of JP2013188299, Feb. 26, 2019 (Year: 2019).*
International Search Report for International Application No. PCT/JP2015/081789 dated Feb. 2, 2016.

* cited by examiner

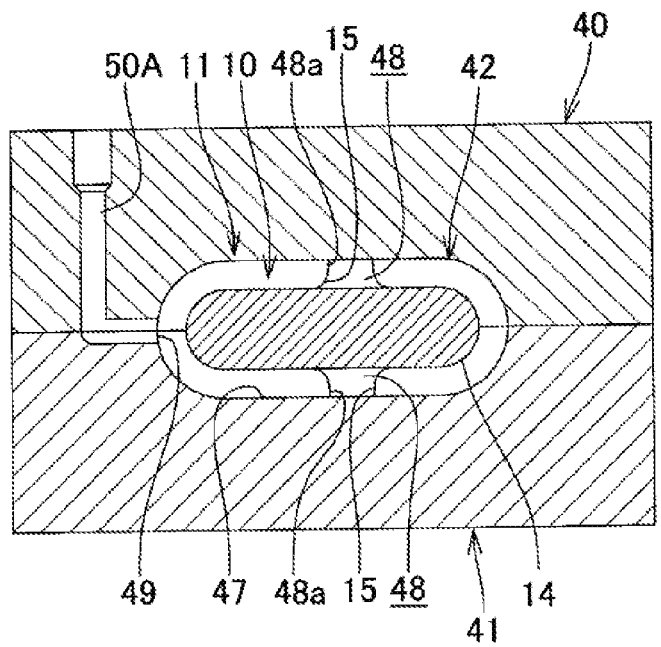
Fig. 10
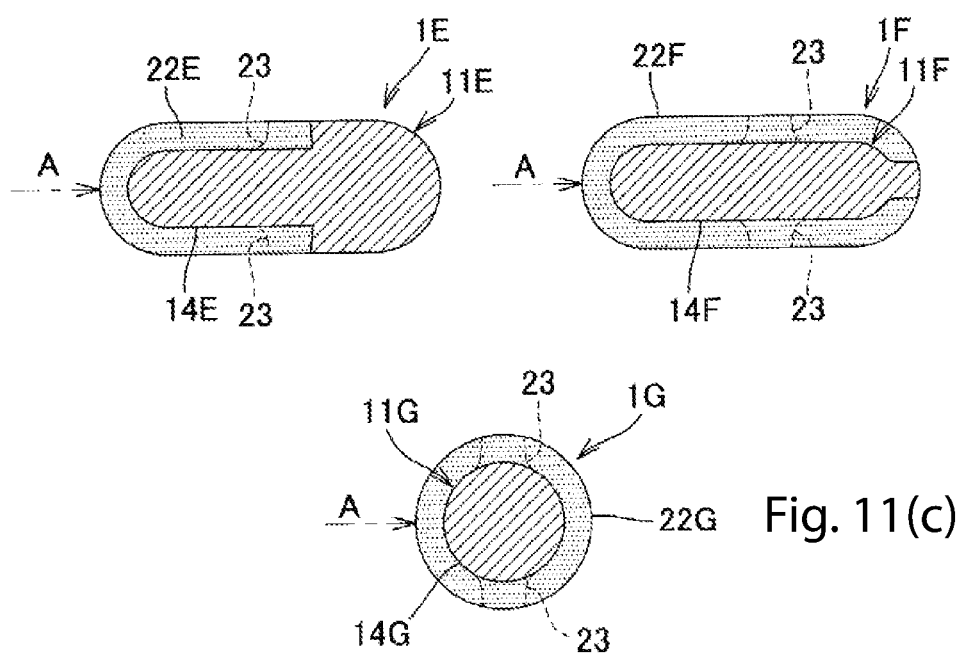
Fig. 11(a)  Fig. 11(b)
Fig. 11(c)

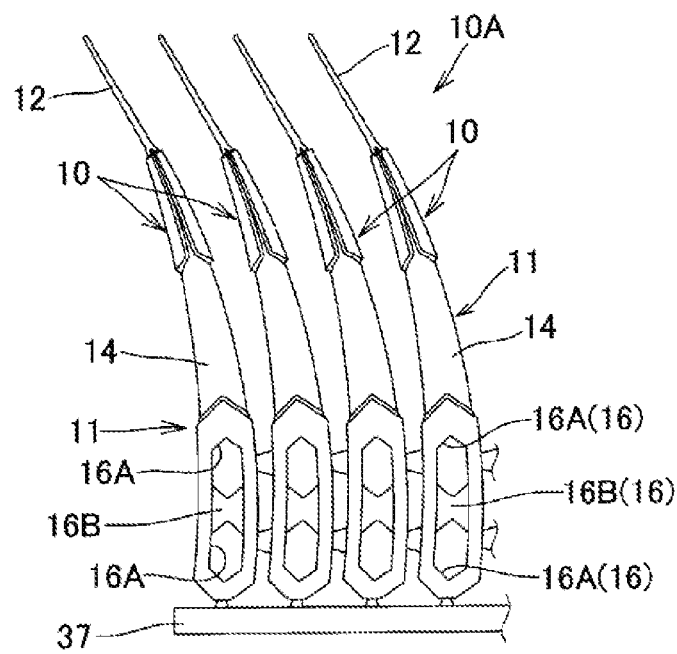
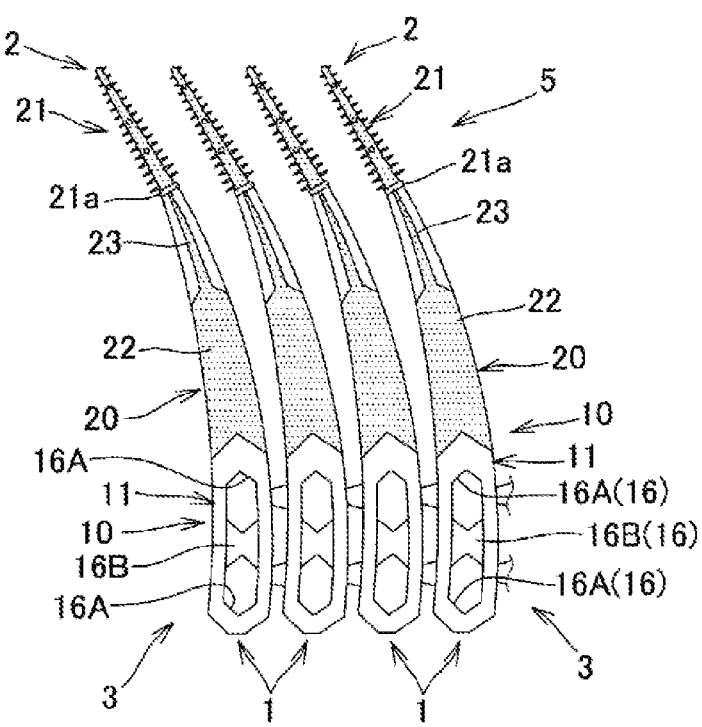

METHOD FOR MANUFACTURING INTERDENTAL CLEANING DEVICE

TECHNICAL FIELD

The present invention relates to a method for manufacturing an interdental cleaning device having an elastomer-covered cleaning portion.

BACKGROUND ART

An interdental cleaning device in actual use includes a base portion made of a synthetic resin and a soft portion made of an elastomer, in which the base portion includes a handle portion and a core portion provided at the front end of the handle portion and having a slender shaft shape, the soft portion includes a cleaning soft portion covering the core portion, the handle portion forms a gripping portion as a grip, and the core portion and the cleaning soft portion form a cleaning portion for cleaning between teeth (see, e.g., Patent Literatures 1 to 3).

A method widely used to manufacture this interdental cleaning device includes charging a synthetic resin material into a first molding space of first molds to form a base portion; placing, in a second molding space of second molds, the base portion molded in the first molds; and charging an elastomeric material into the second molding space to form a soft portion, so that the interdental cleaning device is obtained. In general, a plurality of interdental cleaning devices are also molded simultaneously by a process that includes providing first molds having a plurality of first molding spaces and second molds having the same number of second molding spaces as the first molding spaces; supplying a synthetic resin material to the first molding spaces from a common runner to simultaneously form a plurality of base portions; placing, in the second molding spaces of the second molds, a primary molded product having the base portions connected with a runner; and then charging an elastomeric material into the second molding spaces through a common runner, so that a plurality of interdental cleaning devices are simultaneously formed.

In this regard, the mold structure should be made as simple as possible. Therefore, the elastomeric material is generally charged into each second molding space from the front end side to base end side of the core portion of the base portion, loaded in the second molding space, through a gate placed on the front end side of the interdental cleaning device in the second molding space. In addition, the elastomeric material has relatively high viscosity. Therefore, if the elastomeric material is charged from the base end side to front end side of the core portion during the molding of the cleaning soft portion in the second molding space, poor charging may occur at the front end of the cleaning soft portion. Also from this point, therefore, the elastomeric material is generally charged from the front end side to base end side of the core portion so that poor molding can be prevented at the front end of the cleaning soft portion.

As mentioned above, the method of charging the elastomeric material from the front end side to base end side of the core portion can make the mold structure simple and prevent poor molding at the front end of the cleaning soft portion. However, this method raises problems as described below. When this method is used, the opening area of the gate portion cannot be made large, so that the amount of injection of the elastomer cannot be increased, which can make it impossible to charge a sufficient amount of the elastomeric material into the gripping portion side, make it difficult to form a non-slip portion or other portions on the gripping portion, and lead to a quick decrease in the temperature of the charged elastomer. In this method, therefore, it can be difficult to bond the elastomeric material to the synthetic resin of the core portion, so that the non-slip portion may easily peel off. In order to prevent the front end of the core portion from being softened and deformed, this method also forces the core portion to have a large diameter, which can make it impossible to insert the cleaning portion between teeth or can reduce the length of the cleaning portion insertable between teeth, so that sufficient cleaning ability cannot be obtained.

In this regard, Patent Literature 4 proposes an interdental cleaning device-manufacturing method that includes retaining the elastomeric material in an annular reservoir space formed along the circumference of the handle portion in the second molding space; and supplying the elastomeric material from the reservoir space uniformly to the entire circumference of the base portion of the cleaning portion molding space through a plurality of connecting portion molding spaces formed along the handle portion.

CITATIONS LIST

Patent Literature 1: Japanese Patent No. 4236571
Patent Literature 2: Japanese Patent No. 3002668
Patent Literature 3: Japanese Unexamined PCT Publication No. 2001-506514
Patent Literature 4: Japanese Unexamined Patent Application Publication No. 2013-188299

SUMMARY OF INVENTION

Technical Problems

However, it has been found that even in the manufacturing method described in Patent Literature 4, if the distance between the port for supply of the elastomeric material to the reservoir space and the port for supply of the elastomeric material from the reservoir space to the connecting portion molding space differs depending on the individual connecting portion molding spaces, the elastomeric material can be supplied at different timings to the connecting portion molding spaces. This causes variations to occur in the timing of supply of the elastomeric material from the connecting portion molding spaces to the base portion of the cleaning portion molding space, degrading the quality of the cleaning soft portion and cause variations in the thickness of the elastomer layer on the handle portion. With this, a problem with appearance may occur.

In the manufacturing method described in Patent Literature 4, the second molds have a plurality of second molding spaces formed in parallel, and the elastomeric material is supplied to a runner and then supplied separately to the second molding spaces through a plurality of supply channels. In this supply system, the runner cannot be placed at the mating surfaces of the second molds, which can create the problem of a complicated mold structure and increase elastomeric material waste. It has also been found that since the elastomeric material is sequentially supplied from one end to the other end of the runner, a difference can occur in the elastomeric material supply timing between the one end-side second molding space and the other end-side second molding space, so that variations could occur in the quality of the cleaning soft portion.

It is an object of the present invention to provide an interdental cleaning device-manufacturing method that can improve the quality of a cleaning soft portion through effective utilization of a non-slip portion formed on a handle portion and can also reduce variations between interdental cleaning devices in the quality of the cleaning soft portion and in the quality of the non-slip portion formed to cover the handle portion. It is another object of the present invention to provide an interdental cleaning device manufactured by such a method.

Solutions to Problems

The present invention is directed to a method for manufacturing an interdental cleaning device including: a base portion that is formed by molding a synthetic resin material and includes a handle portion and a core portion provided at a front end of the handle portion and having a slender shaft shape; and a soft portion that is formed on the base portion by molding an elastomeric material, and includes a cleaning soft portion substantially covering at least part of the core portion, a non-slip portion substantially covering at least part of the handle portion, and connecting portions also covering at least part of the handle portion, extending from two sites of the non-slip portion, and being connected to the cleaning soft portion. The method includes: causing a gate of a mold for molding the soft portion to open at a position substantially equally distant from positions of two communicating openings of the non-slip molding space for molding the non-slip portion, the two communicating openings communicating with the connecting portion molding spaces for molding the connecting portions; and charging the elastomeric material from the gate into a soft portion molding space to fill the soft portion molding space.

More specifically, the present invention is directed to a method for manufacturing an interdental cleaning device including a base portion and a soft portion. The base portion is formed by molding a synthetic resin material and including: a handle portion; and a core portion provided at the front end of the handle portion and having a slender shaft shape tapered to decrease in diameter toward the front end side. The soft portion includes: a cleaning soft portion that is formed on the base portion by molding an elastomeric material, substantially covers at least part of the core portion, and includes a cover portion with a thickness of 0.1 mm to 0.3 mm covering the core portion and a plurality of protrusions that are formed with a length of 0.1 mm to 2.0 mm on the cover portion to protrude to the outside and spaced apart from one another in the longitudinal direction; a non-slip portion with a thickness of 0.1 mm to 0.6 mm (more preferably 0.2 to 0.5 mm) substantially covering at least part of the handle portion; and connecting portions also covering at least part of the handle portion, extending from two sites of the non-slip portion, and being connected to the cleaning soft portion. In the interdental cleaning device, the protrusions of the cleaning soft portion are not limited to rod-shaped protrusions, and may be any of various other forms, such as sheet-shaped protrusions extending continuously in the circumference direction and half-disk-shaped protrusions extending over about 180 degrees.

In the manufacturing method, the elastomeric material is supplied from the non-slip portion molding space to the cleaning portion molding space through the connecting portion molding spaces in the process of molding the soft portion after the handle portion is placed in the soft portion molding space. The mold or molds have a gate for injecting the elastomeric material into the mold or molds during the molding of the soft portion. This gate has an opening at a position substantially equally distant from the positions of two communicating openings that are portions of the non-slip portion molding space for molding the non-slip portion and communicate with the connecting portion molding spaces for molding the connecting portions. Therefore, during the molding of the soft portion, the elastomeric material supplied from the gate to the non-slip portion molding space can be supplied simultaneously to the connecting portion molding spaces from the non-slip portion molding space. Therefore, the elastomeric material can be supplied at the same timing from the connecting portion molding spaces to the cleaning portion molding space, which will effectively prevent poor molding of the cleaning soft portion and improve the quality of the interdental cleaning device. In addition, since the elastomeric material is charged from the base side of the core portion, the non-slip portion can be smoothly molded on the handle portion. In addition, the elastomeric material is charged from the base side of the core portion with a large cross-section, which makes it possible to prevent the core portion from being deformed by heat during the charging of the elastomeric material and to allow the front end portion of the core portion to have a small diameter, so that the length of the cleaning portion insertable between teeth can be made as large as possible to increase the ability to clean the space between teeth. In addition, the interdental cleaning device manufactured by this method has the non-slip portion and the connecting portions formed of the elastomeric material on the handle portion. The non-slip portion and the connecting portions allow the interdental cleaning device to have improved handleability.

In a preferred embodiment of the present invention, the connecting portion molding spaces are located to connect and communicate with two sites that are substantially symmetrically apart by substantially 180 degrees in a circumferential direction about a central axis of a cleaning soft portion molding space for molding the cleaning soft portion. As long as the gate is placed at a middle position equally distant from the two communicating holes, the elastomeric material can be supplied at the same timing to the two communicating holes even if the cleaning soft portion molding space makes an angle other than 180 degrees in the circumferential direction with the central axis. However, when the cleaning soft portion molding space makes an angle of 180 degrees in the circumferential direction with the central axis, the elastomeric material can be supplied precisely at the same timing from the two connecting portion molding spaces to the cleaning portion molding space, which makes it possible to further effectively prevent poor molding of the cleaning portion. In addition, the connecting portions are symmetrically disposed, which can improve the design quality of the interdental cleaning device and improve the handleability at the time when the device is held by being pinched at the connecting portions.

In a preferred embodiment, the mold has a cleaning soft portion base end portion molding space that is for molding a loop-shaped cleaning soft portion base end portion and is located at a base end of the cleaning soft portion molding space, and the connecting portion molding spaces are located to connect and communicate with two sites of the cleaning soft portion base end portion molding space. This structure allows the cleaning soft portion base end portion molding space to function as an elastomeric material reservoir space, so that the elastomeric material supplied from the connecting portion molding spaces can be transiently retained in the cleaning soft portion base end portion molding space and then supplied to the front end of the cleaning portion molding space. This makes it possible to supply the elastomeric material from the base end to front ends of the cleaning portion molding space uniformly over the entire circumference, so that poor molding of the cleaning soft portion can be further effectively prevented. In addition, the interdental cleaning device manufactured by this method has the cleaning soft portion base end portion, which is formed by molding the elastomer in the cleaning soft portion base end portion molding space. The cleaning soft portion base end portion will function as an insertion limiting portion for limiting the maximum length of insertion of the cleaning portion into the space between teeth, which makes it possible to avoid an excessive insertion-induced load on the core portion, so that the buckling of the shank can be prevented and a gum massage effect can also be expected when the cleaning soft portion base end portion is brought into contact with the gum.

In a preferred embodiment, the handle portion is formed in a substantially flat rod shape, the connecting portion molding spaces are placed at positions facing both wide surfaces of the handle portion, and the opening of the gate is placed at a position facing a narrow surface of the handle portion. According to this configuration, the connecting portion molding spaces can be made wide so that a sufficient amount of the elastomeric material can be supplied to the cleaning portion molding space, which make it possible to further effectively prevent poor molding of the cleaning soft portion. In addition, during use, the interdental cleaning device can be handled for cleaning by being pinched at both wide surfaces of the handle or non-slip portion with thumb and index finger, and thus, the interdental cleaning device can be easily held. In addition, the connecting portion molding spaces allow the molding of the elastomer to form connecting portions on both wide surfaces of the handle portion. Therefore, not only the non-slip portion but also the connecting portions can prevent slipping from the gripping fingers, which leads to improvement of the handleability of the interdental cleaning device and thus is preferred. In addition, no gate mark will be left on both wide surfaces of the non-slip portion. Therefore, even when a design pattern such as a logo or an abstract pattern is formed on both wide surfaces of the non-slip portion, for example, by exposing part of the base portion, any gate mark, which would have an adverse effect on the design pattern, will not be left, so that good appearance and improved design flexibility can be achieved.

In a preferred embodiment, the soft portion molding space is provided in such a manner that the opening of the gate is located at mating surfaces of molds including the mold, and the elastomeric material is charged into the soft portion molding space through the gate formed along the mating surfaces. According to this configuration, the channel for supplying the elastomeric material to the soft portion molding space can be placed at the mating surfaces, which can make the mold structure simple and reduce the length of the elastomeric material supply channel so that the waste of the elastomeric material can be reduced.

In a preferred embodiment, the mold has a plurality of molding spaces arranged in parallel each for molding the soft portion, the mold has a common supply channel for supplying the elastomeric material to both of adjacent non-slip portion molding spaces, which constitute a pair of two of the molding spaces arranged in parallel, the common supply channel extending to a substantially central position between the adjacent non-slip portion molding spaces, the mold has individual supply channels that are branched from the substantially central position and formed to reach openings of the gates formed at opposed positions of the respective non-slip portion molding spaces, and the elastomeric material is charged into each of the molding spaces through the common supply channel and the individual supply channels so that soft portions including the soft portion are simultaneously molded on a plurality of base portions including the base portion. In this case, when the elastomeric material is supplied at substantially the same timing from the non-slip portion molding space to the two communicating openings of the connecting portion molding spaces, the elastomeric material can be supplied at the same timing from the connecting portion molding spaces to the base portion of the cleaning portion molding space, which makes it possible to improve the quality of the non-slip portion and the cleaning soft portion. In addition, the parallel arrangement of the soft portion molding spaces in the mold or molds makes it possible to simultaneously mold a plurality of interdental cleaning devices and thus to manufacture the interdental cleaning devices with improved productivity. In addition, when the common supply channel for supplying the elastomeric material is formed to extend to a substantially central position between the pair of adjacent non-slip portion molding spaces, the elastomeric material can be supplied at substantially the same timing to both molding spaces, so that variations in the quality of the cleaning soft portion can be reduced to half of those in a case where the molding spaces are each individually provided with an elastomeric material supply channel.

A region having a through or bottomed hole may be provided on the handle portion in a range from a base end side to a non-slip portion-covered region. In this case, the amount of the synthetic resin material for the base portion can be reduced, and the presence of such a hole on the gripping portion base end side of the completed interdental cleaning device makes it possible to improve gripability and designability (to increase variety). Similarly to a runner, such a hole will also function as an effective alignment portion for stable loading of the base portion at a proper position in the molding space, when the base portion is placed in the second molding space and then the soft portion is molded thereon. Therefore, such a hole is effective in preventing poor molding of the soft portion.

Advantageous Effects of Invention

The method according to the present invention for manufacturing an interdental cleaning device includes placing a handle portion in a soft portion molding space and then molding a soft portion on the handle portion. In the step of molding the soft portion, an elastomeric material is supplied to a cleaning portion molding space through a non-slip portion molding space and connecting portion molding spaces. This step is performed by causing a gate of a mold for molding the soft portion to open at a position substantially equally distant from positions of two communicating openings of the non-slip molding space for molding the non-slip portion, the two communicating openings communicating with the connecting portion molding spaces for molding the connecting portions; and charging the elastomeric material from the gate into the soft portion molding space. Therefore, when supplied from the gate to the non-slip portion molding space, the elastomeric material can be supplied simultaneously to the connecting portion molding spaces from the non-slip portion molding space. Therefore, the elastomeric material can be supplied to the cleaning portion molding space at the same timing from the connecting portion molding spaces, which makes it possible to effectively prevent poor molding of the cleaning soft portion and to improve the quality of the interdental cleaning device. In addition, the elastomeric material is charged from the base side of the core portion, which makes it possible to smoothly mold the non-slip portion on the handle portion. In addition, the elastomeric material is charged from the base side of the core portion with a large cross-section, which makes it possible to prevent the core portion from being deformed by heat during the charging of the elastomeric material and to allow the front end portion of the core portion to have a small diameter, so that the length of the cleaning portion insertable between teeth can be made as large as possible to increase the ability to clean the space between teeth. In addition, the interdental cleaning device manufactured by this method has the non-slip portion and the connecting portions, which are formed of the elastomeric material on the handle portion. The non-slip portion and the connecting portions allow the interdental cleaning device to have improved handleability.

BRIEF DESCRIPTION OF DRAWINGS

FIG. 10 is a view of second molds with another structure as an alternative version of that of FIG. 9.

FIGS. 11(a) to 11(c) are longitudinal sectional views of non-slip portions of interdental cleaning devices with other structures.

FIG. 15(a) is a front view illustrating a modified example of a primary molded product having holes, and FIG. 15(b) is a front view illustrating a modified example of an interdental cleaning device chain having holes in the same manner.

DESCRIPTION OF EMBODIMENTS

<Interdental Cleaning Device>

First, the configurations of an interdental cleaning device 1 will be described.

Figure 1:
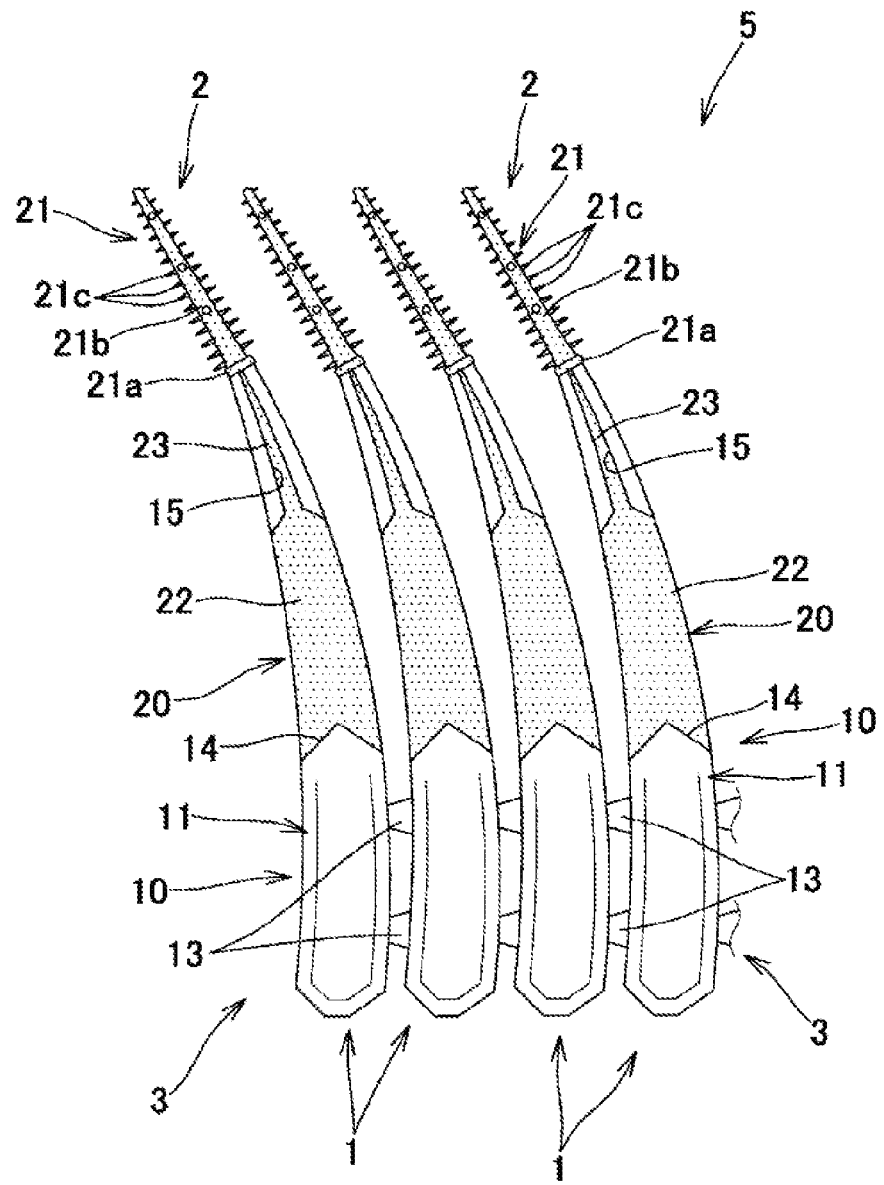
FIG. 1 is a front view of an interdental cleaning device chain.
Figure 2:
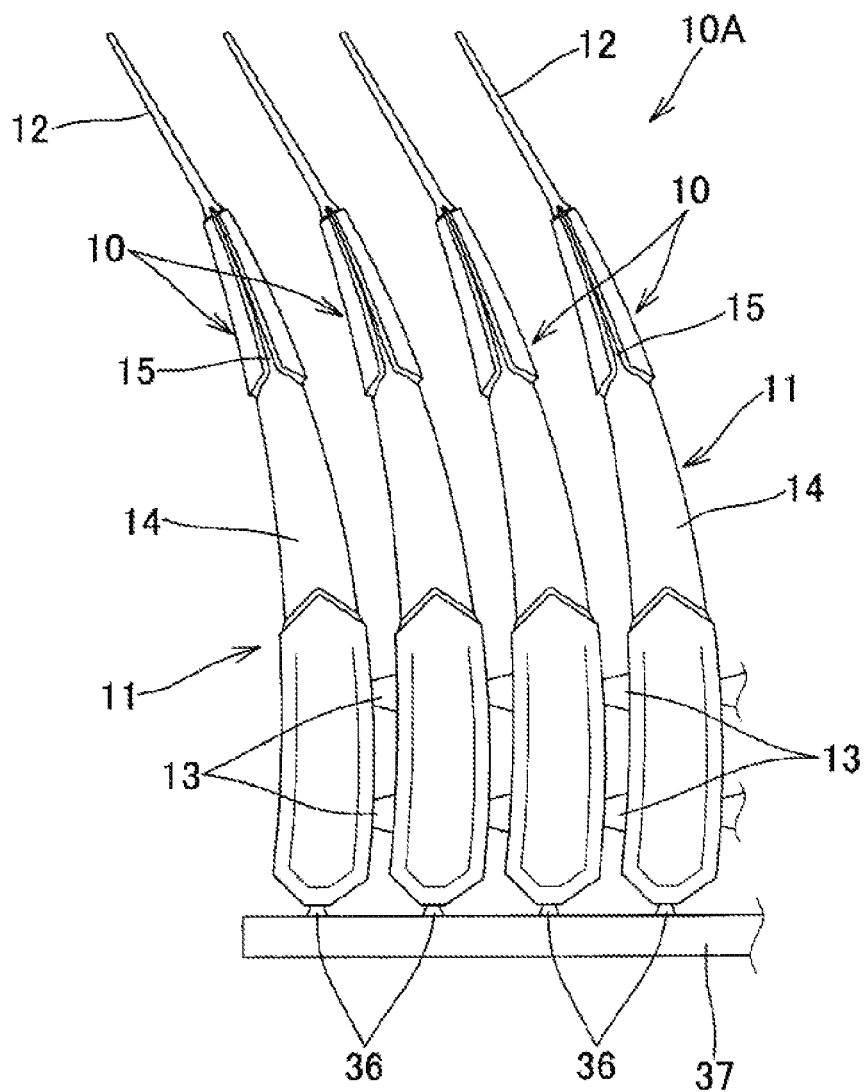
FIG. 2 is a front view of a primary molded product having base portions connected to one another.

As illustrated in FIGS. 1 and 2, the interdental cleaning device 1 includes a cleaning portion 2 for interdental cleaning and a gripping portion 3 as a handle, which are distinguishable in terms of function, and also includes a base portion 10 including a synthetic resin and a soft portion 20 including an elastomeric material, which are distinguishable in terms of material. The interdental cleaning devices 1 are manufactured in the form of an interdental cleaning device chain 5, which includes a plurality of interdental cleaning devices 1 separably connected in parallel to one another. The user will use each interdental cleaning device 1 by disconnecting one by one the interdental cleaning devices 1 at connecting protrusions 13 from one side of the interdental cleaning device chain 5. The number of connected interdental cleaning devices 1 in the interdental cleaning device chain 5 may be selected freely.

(Base Portion)

The base portion 10 includes a synthetic resin. As illustrated in FIGS. 1 and 2, the base portion 10 includes a handle portion 11 that forms the gripping portion 3 and has a flat rod shape (a slender plate shape), a core portion 12 that is connected to the front end of the handle portion 11 and has a slender shaft shape, and connecting protrusions 13 provided to separably connect the adjacent handle portions 11. A plurality of the base portions 10 are arranged in parallel and connected together with the connecting protrusions 13 to form a primary molded product 10A. In the drawings, reference sign 37 represents a first runner portion for the interdental cleaning devices 1.

Figure 12:
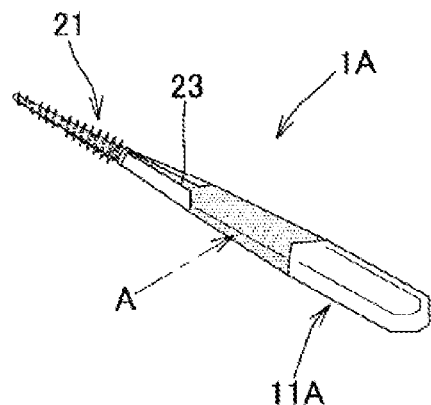
FIGS. 12(a) to 12(d) are perspective views of interdental cleaning devices with other structures.
Figure 12:
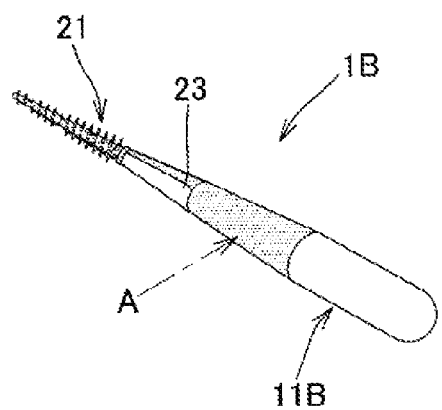
Figure 12:
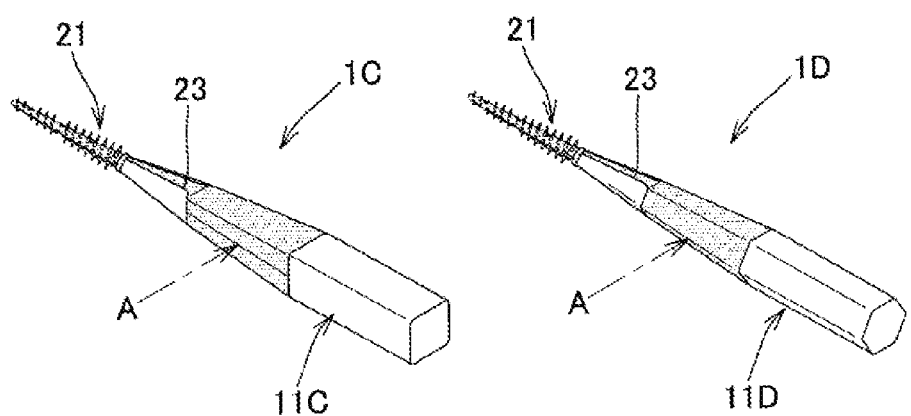

The handle portion 11 is formed in a gently-curved, flat, rod shape (slender plate shape). Alternatively, the handle portion 11 may be formed in any other shape for facilitating the gripping by hand and the interdental cleaning. For example, the handle portion 11 may also be formed in a linear, flat, slender plate shape like the handle portion 11A of the interdental cleaning device 1A shown in FIG. 12(a), a rod shape with a circular cross-section like the handle portion 11B of the interdental cleaning device 1B shown in FIG. 12(b), a rod shape with a square cross-section like the handle portion 11C of the interdental cleaning device 1C shown in FIG. 12(c), a rod shape with a hexagonal cross-section like the handle portion 11D of the interdental cleaning device 1D shown in FIG. 12(d), or other rod shapes with a circular, elliptical, or polygonal cross-section. The front end portion of the handle portion 11 becomes narrower in width toward the core portion 12 side, and is smoothly connected to the core portion 12. The dimensions of the handle portion 11 may be selected freely as long as they can facilitate the gripping by hand and the interdental cleaning. In the case of the flat rod shape, its width (the width viewed from the wide side) is preferably up to 3.0 to 10 mm, its thickness (the width viewed from the narrow side) is preferably up to 0.8 to 5.0 mm, and the ratio of the width to the thickness (width/thickness) is preferably 1.0 to 10.

The core portion 12 is formed in a substantially-linear, slender shaft shape. The core portion 12, which is to be covered with an elastomeric material, is gently tapered to decrease in diameter toward the front end side. In this regard, the taper angle of the core portion 12 may be constant over the entire length of the core portion 12 or may be continuously or gradually reduced toward the front end side of the core portion 12.

As illustrated in FIGS. 1 and 2, the connecting protrusions 13 between the adjacent handle portions 11 are integrally formed with the handle portions 11. A pair of the connecting protrusions 13 are provided at base and front end sides of each handle portion 11 with a certain spacing between them in the longitudinal direction. The connecting protrusions 13 are formed in an isosceles trapezoid shape when viewed from the front side. The number of the connecting protrusions 13 may be selected freely. Alternatively, for example, only one connecting protrusion may be provided, as described later (see FIGS. 13 and 14).

Examples of synthetic resin materials that can be used to form the base portion 10 include polypropylene (PP), polybutylene terephthalate (PBT), polyethylene, polyethylene terephthalate, polycyclohexylene dimethylene terephthalate, saturated polyester resins, polymethyl methacrylate, cellulose propionate, polyurethane, polyamide, polycarbonate, ABS (acrylonitrile-butadiene-styrene) resins, and other thermoplastic synthetic resin materials. In particular, polypropylene (PP), polybutylene terephthalate (PBT), and polyamide are preferred, which can prevent the base portion 10 from buckling. Polypropylene is most preferred, which can be molded at low temperatures, can reduce cycle time and improve productivity, and can be processed with a lower thermal load on the molding facility. In addition, fiber materials such as glass fibers, carbon fibers, or aramid fibers are also preferably added to the synthetic resin material used to form the base portion 10. The addition of fiber materials can improve the dimensional stability of the base portion 10 and increase the strength and stiffness of the base portion 10 to prevent deformation, which also makes it possible to prevent poor loading when the molded base portion 10 is loaded into a second molding space 42 of second molds 40 and 41. In addition, the addition of fiber materials can increase the thermal deformation temperature of the core portion 12. Therefore, the core portion 12 can be effectively prevented from being softened and deformed by heat from the elastomeric material during the molding of a cleaning soft portion 21. In addition, the fiber materials can increase the strength and stiffness, which makes it possible to prevent the deformation of the core portion 12 due to the elastomeric material injection pressure and to effectively prevent poor molding of the cleaning soft portion 21.

(Soft Portion)

As illustrated in FIG. 1, the soft portion 20, which is molded integrally with the base portion 10 using an elastomeric material, includes a cleaning soft portion 21 covering the core portion 12, a non-slip portion 22 covering the base end side of the handle portion 11, and a pair of connecting portions 23 extending from two sites of the non-slip portion 22, being connected to the cleaning soft portion 21, and covering the front end side of the handle portion 11.

The cleaning soft portion 21 includes a loop-shaped insertion limiting portion (which corresponds to the base end of the cleaning soft portion) 21a provided at the base end to limit the insertion between teeth, a cover portion 21b extending from the insertion limiting portion 21a to the front end side and covering the core portion 12, and a plurality of protrusions 21c that are formed on the cover portion 21b to protrude to the outside and spaced apart from one another in the longitudinal direction.

The insertion limiting portion 21a is formed in a ring shape at the base end of the core portion 12 to extend continuously along the entire circumference of the base end of the cover portion 21b and to protrude outside the cover portion 21b. The insertion limiting portion 21a is configured to limit the maximum length of insertion of the cleaning portion 2 into the space between teeth. In addition, the insertion limiting portion 21a is made of an elastomeric material so that a gum massage effect can also be expected when the insertion limiting portion 21a is brought into contact with the gum. The thickness and width of the insertion limiting portion 21a may be selected freely. In order to prevent poor molding of the cleaning soft portion 21, for example, the insertion limiting portion 21a preferably has a thickness of 0.1 mm to 2.5 mm and a width of 1.2 mm to 3.0 mm.

The cover portion 21b preferably has a thickness of 0.1 mm to 0.3 mm. This is because if the cover portion 21b is too thick, it will have a large diameter, which will reduce the insertability into the space between teeth, and if the cover portion 21b is too thin, it will be impossible to charge the elastomeric material until the front end of the cleaning portion 2 can be completed. The thickness of the cover portion 21b is also preferably smaller than that of the elastomer of the non-slip portion 22. These features will make it easy to generate frictional heat during the injection of the elastomeric material from a non-slip portion molding space 47 into a cleaning soft portion molding space 46 through connecting portion molding spaces 48. The generated frictional heat can melt the interface between the core portion 12 and the elastomeric material in the cleaning soft portion 21, so that the cleaning soft portion 21 can have high adhesion.

Figure 16:
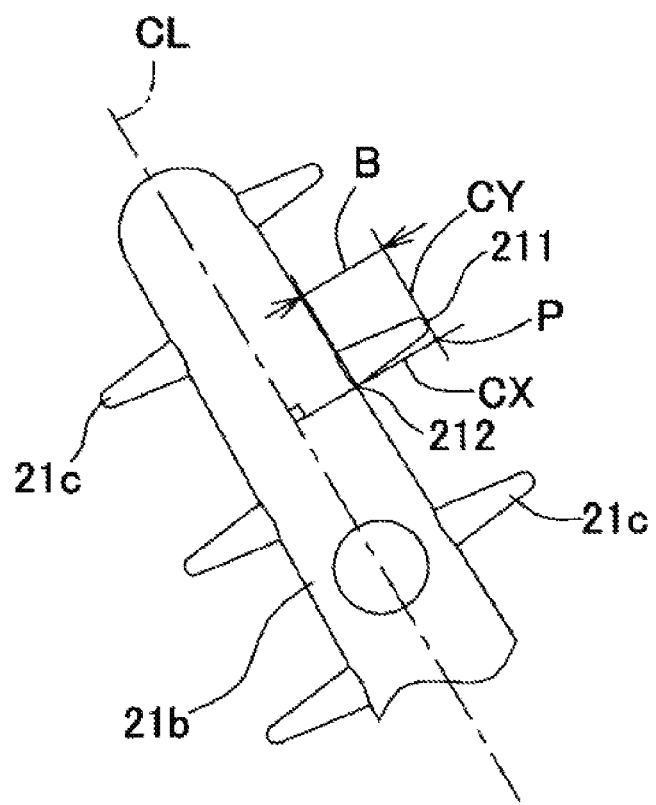
FIG. 16 is a diagram illustrating the length of a protrusion.

The protrusions 21c are formed apart from one another in the longitudinal direction of the cover portion 21b and also arranged apart from one another in the circumferential direction of the cover portion 21b. The cross-sectional area of the base end of the protrusion 21c, the length and number of the protrusions 21c, and the pitch at which the protrusions 21c are arranged may be selected freely. In view of the moldability or the cleaning ability, the cross-sectional area of the base end of the protrusion 21c is preferably from about 0.03 mm$^2$ to about 1.5 mm$^2$, the length of the protrusion 21c is preferably from about 0.1 mm to about 2.0 mm, the number of the protrusions 21c is preferably from 20 to 100, and the protrusions 21c are preferably arranged at a pitch of 0.1 mm to 1.5 mm. In this context, the length B of the protrusion 21c means, as shown in FIG. 16, the distance between a rear end 212 and a point P, wherein the rear end 212 is the rearmost end (on the handle portion 11 side) of the junction between the protrusion 21c and the cover portion 21b, and the point P is the point of intersection between lines CX and CY. The line CX is perpendicular to a center line CL of the core portion 12, and the line CY is parallel to the center line CL of the core portion 12 and passes through a top 211 of the protrusion 21c, which is most distant from the center line CL. In this example, the protrusions 21c used are specifically conical rod-shaped. It will be understood that this example is non-limiting and their cross-section may have any shape other than a circle, such as an ellipse or a polygon. The protrusions 21c may also have any shape other than a rod shape, such as a tapered axially-flat shape or a half-disk shape extending continuously in the circumferential direction.

The non-slip portion 22 is an exterior portion formed by filling, with an elastomeric material, a loop-shaped concave portion 14 formed at a lengthwise middle portion of the handle portion 11. The width of the non-slip portion 22 may be selected freely. If the non-slip portion 22 is too thin, poor filling with the elastomeric material may occur, and if it is too thick, the gripping portion 3 can give an odd feel when gripped by fingers. Therefore, the non-slip portion 22 preferably has a thickness of 0.1 mm to 0.6 mm, more preferably 0.2 to 0.5 mm. As mentioned above, the non-slip portion 22 is formed by filling the loop-shaped concave portion 14. Therefore, the non-slip portion 22 is configured not to peel.

The connecting portions 23 are formed at widthwise central portions of both wide surfaces on the front end side of the handle portion 11. The connecting portions 23 are formed at two sites, which are located symmetrically apart by 180 degrees in the circumferential direction about the central axis of the front end portion of the handle portion 11. The connecting portions 23 are formed by filling, with an elastomeric material, a pair of linear grooves 15 formed at the front end side of the handle portion 11. It will be understood that the connecting portions 23 do not always have to be provided at widthwise central portions and may be provided at any widthwise portions as long as they are located at positions opposed with a shortest distance between them on both wide surfaces of the front end portion of the handle portion 11.

The connecting portions 23 are provided to supply the elastomeric material from the non-slip portion 22 to the cleaning soft portion 21 during the molding of the soft portion 20. The width of the connecting portions 23 may be selected freely. If the connecting portions 23 are too narrow, poor filling with the elastomeric material can easily occur during the molding of the soft portion 20. Therefore, the connecting portions 23 preferably have a width of 0.1 mm or more.

Examples of elastomeric materials that can be used to form the soft portion 20 include thermoplastic elastomer materials including styrenes, olefins, and polyamides; and thermosetting elastomer materials such as silicone rubbers, urethane rubbers, fluororubbers, natural rubbers, and synthetic rubbers. Particularly preferred are materials having compatibility with the synthetic resin material included in the base portion 10. For example, when the base portion 10 is made of polypropylene, the soft portion 20 should preferably be made of a polyolefin-based elastomeric material or a styrene-based elastomeric material.

<Manufacturing Method>

Next, a method for manufacturing the interdental cleaning device 1 will be described.

As illustrated in FIG. 3A, FIG. 3B, FIG. 4, FIG. 7A, FIG. 7B, FIG. 8 and FIG. 9, the method for manufacturing the interdental cleaning device 1 includes a base portion molding step including charging a synthetic resin material into first molding spaces 32 of first molds 30 and 31 to form base portions 10; and a soft portion molding step including placing, in second molding spaces 42 of second molds 40 and 41, the base portions 10 molded in the first molds 30 and 31 and then charging an elastomeric material into the second molding spaces 42 to form soft portions 20.

(Base Portion Molding Step)

Figure 3A:
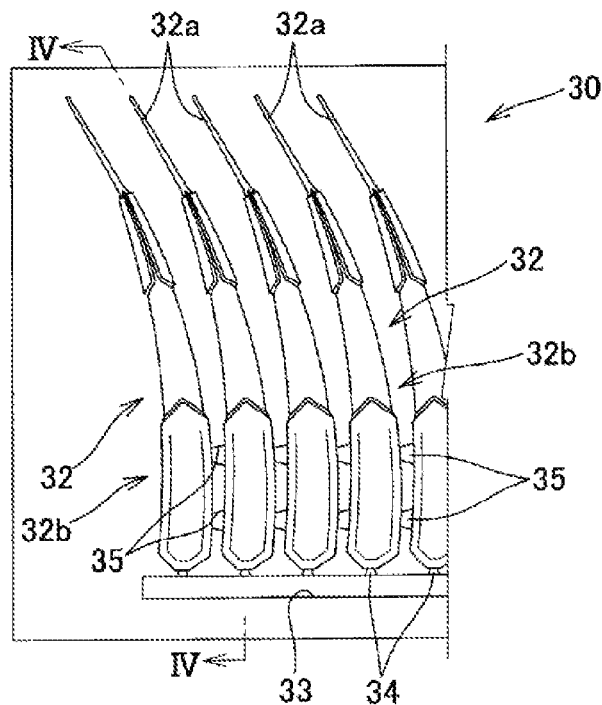
FIG. 3(a) is a front view of the mating surface of one first mold.
Figure 3B:
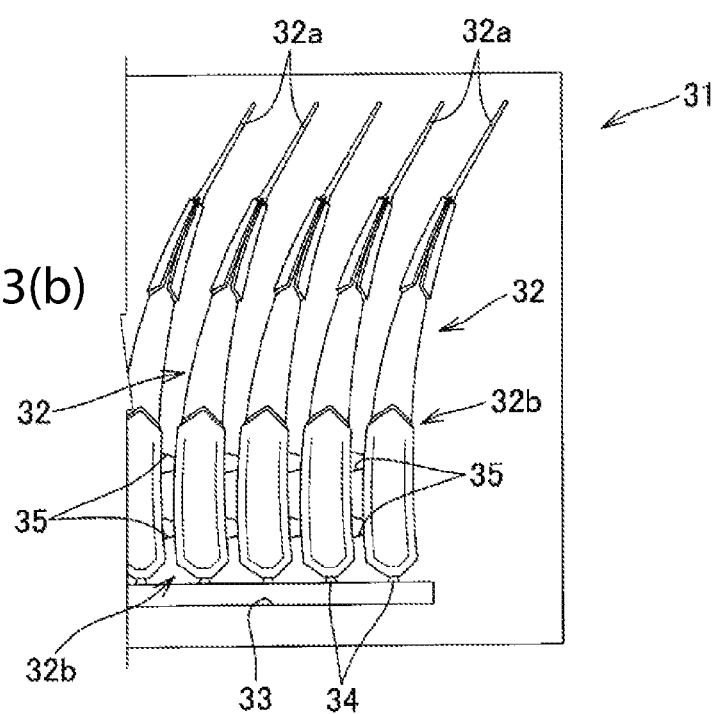
FIG. 3(b) is a front view of the mating surface of the other first mold.
Figure 4:
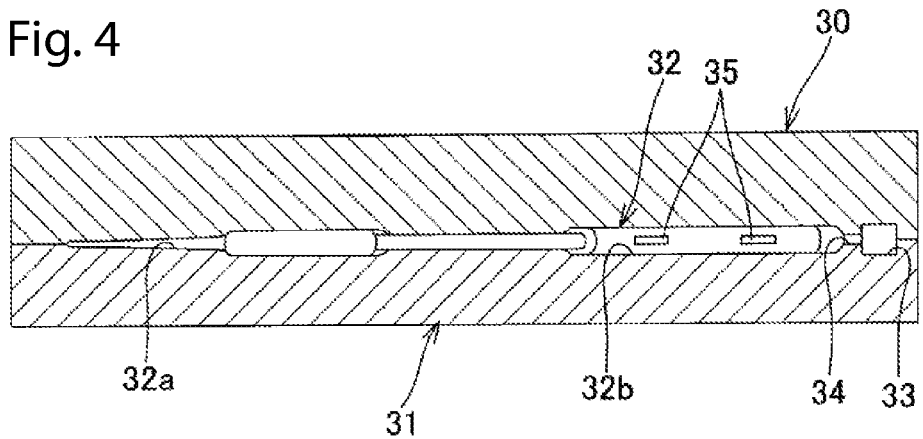
FIG. 4 is a longitudinal sectional view of the closed first molds along the IV-IV line in FIG. 3(a).

As illustrated in FIG. 3A, FIG. 3B and FIG. 4, the base portion molding step includes charging a synthetic resin material into first molding spaces 32 of first molds 30 and 31 to form base portions 10. More specifically, the first molds 30 and 31 used have a plurality of first molding spaces 32 formed in parallel and each having a core portion molding portion 32a and a handle portion molding portion 32b; a pair of connecting protrusion molding portions 35 each formed between adjacent handle portion molding portions 32b to communicate therewith; a first runner 33 formed on the base end side of the first molding spaces 32; and first gates 34 through which the first molding spaces 32 communicate with the first runner 33. When supplied to the first runner 33, a synthetic resin material containing fibers is allowed to pass through the first gates 34 and charged into the first molding spaces 32 to simultaneously mold a plurality of base portions 10. Thus, a primary molded product 10A is formed, which includes the base portions 10, a first runner portion 37, first gate portions 36, and connecting protrusions 13. The base portions 10 may be molded one by one. However, the simultaneous molding of a plurality of base portions 10 makes it possible to improve productivity and to transfer the base portions 10 at the same time by holding the molded first runner portion 37, which can improve workability and thus is preferred. Each first gate 34 may be formed at any position on the base end side opposite to the core portion molding portion 32a of the first molding space 32, more preferably, at any position from the connecting protrusion molding portion 35 to the base end side, on the base end side opposite to the core portion molding portion 32a of the first molding space 32. However, a side gate should preferably be formed as the first gate 34 at the base end of the first molding space 32, so that the risk of causing the first gate portions 36 of the primary molded product 10A to be pinched between the second molds 40 and 41 can be reduced in the process of loading the primary molded product 10A into the second molds 40 and 41. Alternatively, a hot runner may be provided instead of the first runner 33 including a cold runner in the first molds 30 and 31. However, the hot runner can make the molds 30 and 31 large and increase manufacturing costs. Therefore, it is preferred to provide the first runner 33 including a cold runner. In addition, the base portions 10 can be stably connected by the first runner portion 37, which can improve the handleability of the primary molded product 10A in the process of transferring the primary molded product 10A into the second molds 40 and 41 and thus is preferred. In addition, when each first gate 34 has, for example, a cylindrical or spindle shape with a diameter of 0.1 to 3.0 mm, a cold runner can be used, and the first gates 34 can be arranged at narrow intervals, which can make the molded product small and thus is preferred.

Any number of connecting protrusion molding portions 35 may be provided, and only one connecting protrusion molding portion 35 may also be provided. However, two or more connecting protrusion molding portions 35 should preferably be provided apart from each other in the longitudinal direction of the handle portion molding portion 32b for the following reasons. The base portions 10 should be connected to one another through the first runner portion 37 by leaving the first runner portion 37 and the first gate portions 36 unremoved as in the modified examples (FIGS. 13 and 14) described below. If the base portions 10 are connected by only one connecting protrusion, the adjacent base portions 10 can fail to be connected with sufficient strength, so that when the molds are opened after the molding of the base portions 10, the base portions 10 can move relative to one another, which can cause the breakage of the connecting protrusion 13, separate the base portions 10 from one another, and thus make the molding impossible. In addition, the connecting protrusion 13 can buckle, which will make it impossible to load the base portions 10 at appropriate positions in the second molding spaces 42 or cause poor molding or poor handleability such as unintentional detachment of other interdental cleaning devices during use.

In the base portion molding step, when the synthetic resin material containing fibers is supplied simultaneously to a plurality of first molding spaces 32, respectively, from the first gates 34 on the base end side from the connecting protrusion molding portion 35 of the first molding space 32, the fibers will be oriented in the longitudinal direction of the first molding spaces 32, namely, in the longitudinal direction of the base portions 10, which makes it possible to improve the bending strength or axial buckling strength of the base portions 10 and to effectively prevent the core portion 12 from bending or buckling during use of the interdental cleaning device 1. In addition, the fibers can also improve the dimensional stability of the base portions 10 and increase the strength and stiffness to prevent the deformation of the base portions 10, which makes it possible to prevent poor loading in the process of loading the molded base portions 10 into the second molding spaces 42 of the second molds 40 and 41. The fibers can also raise the thermal deformation temperature of the core portions 12, which makes it possible to effectively prevent the core portions 12 from being softened and deformed by heat from the elastomeric material during the molding of the cleaning soft portions 21. The fibers can also increase the strength and stiffness of the core portions 12, which makes it possible to prevent the core portions 12 from being deformed by the elastomeric material injection pressure. In this way, the deformation of the core portions 12 can be prevented in the process of molding the cleaning soft portions 21. This makes it possible to more effectively prevent poor molding of the cleaning soft portions 21.

(Soft Portion Molding Step)

Figure 5:
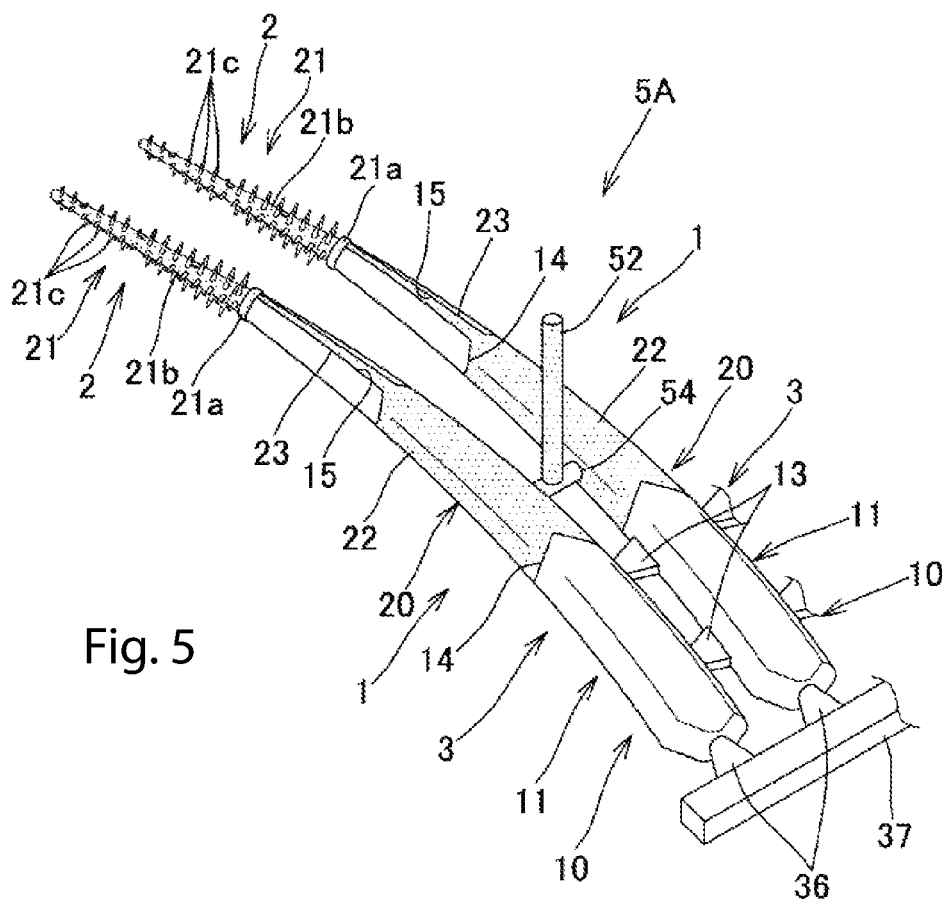
FIG. 5 is a perspective view of an interdental cleaning device chain molded with second molds.
Figure 6:
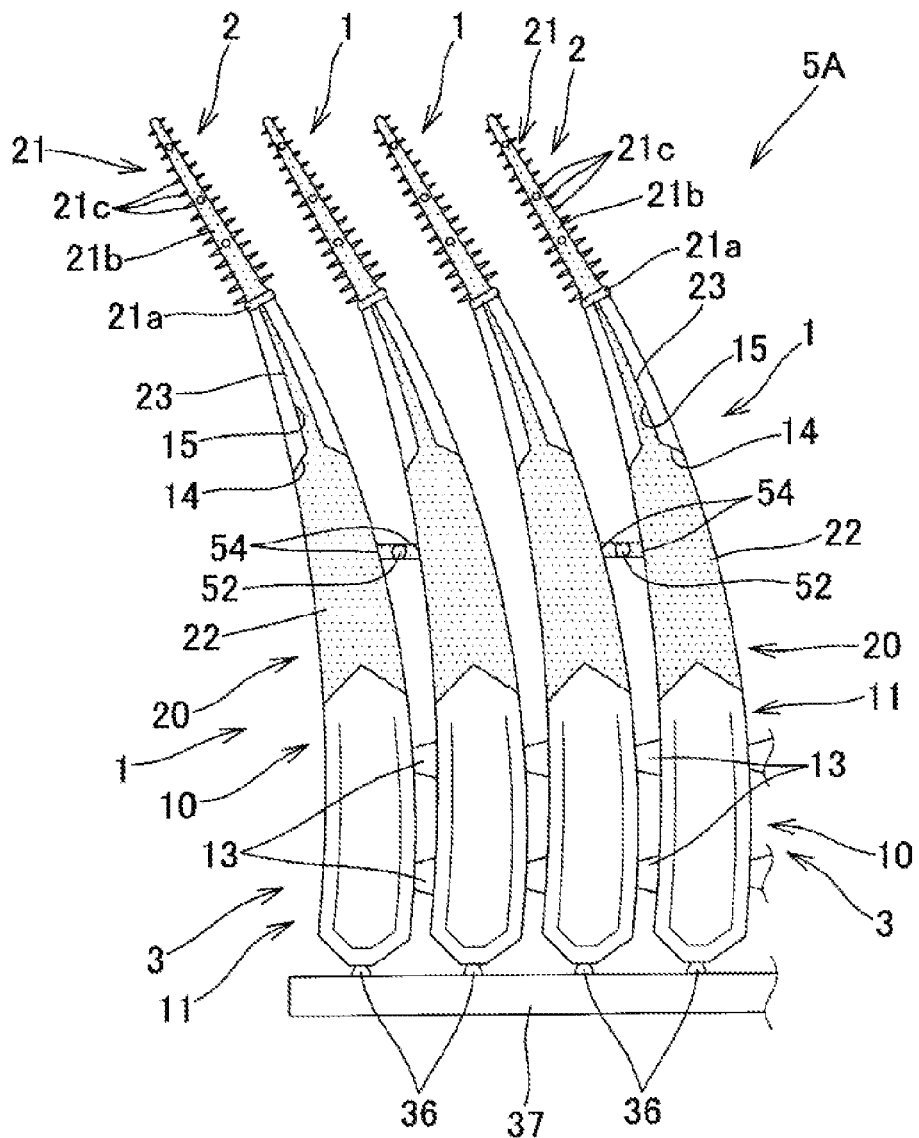
FIG. 6 is a front view of the interdental cleaning device chain.
Figure 7A:
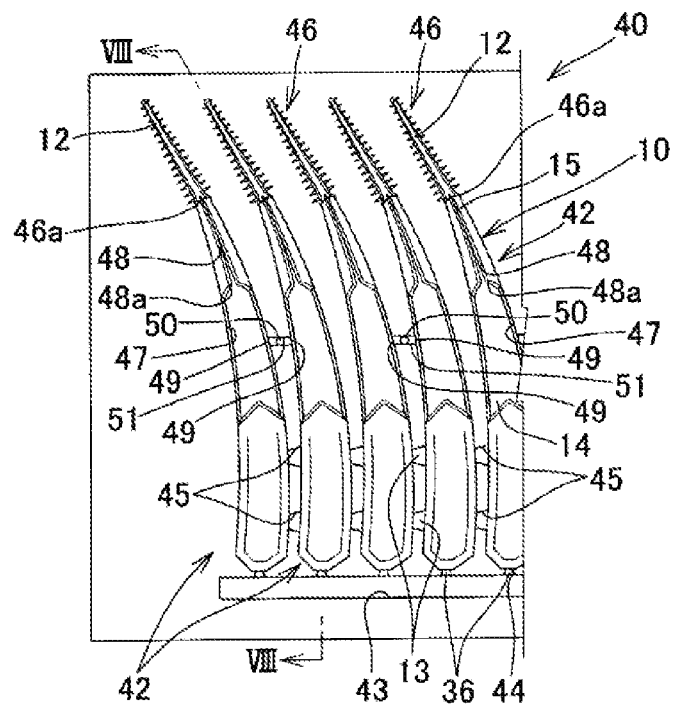
FIG. 7(a) is a front view of the mating surface of one second mold.
Figure 7B:
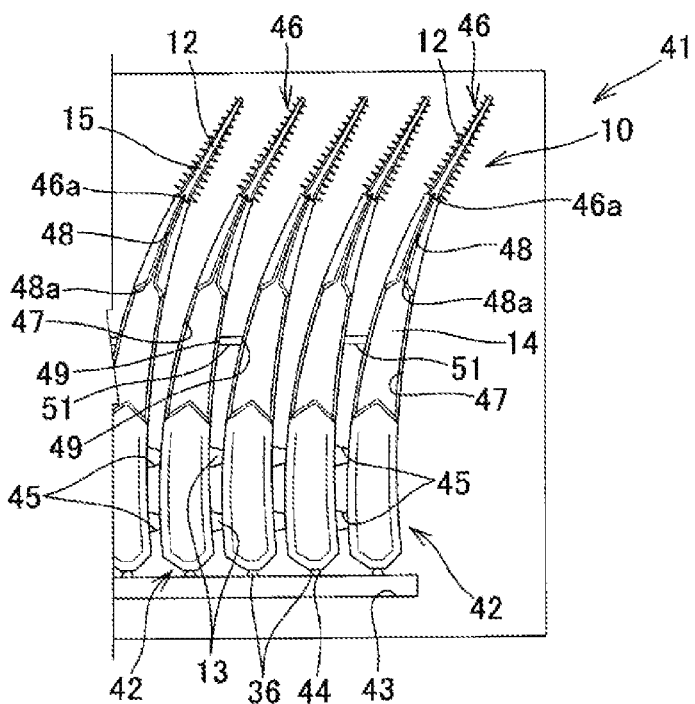
FIG. 7(b) is a front view of the mating surface of the other second mold.
Figure 8:
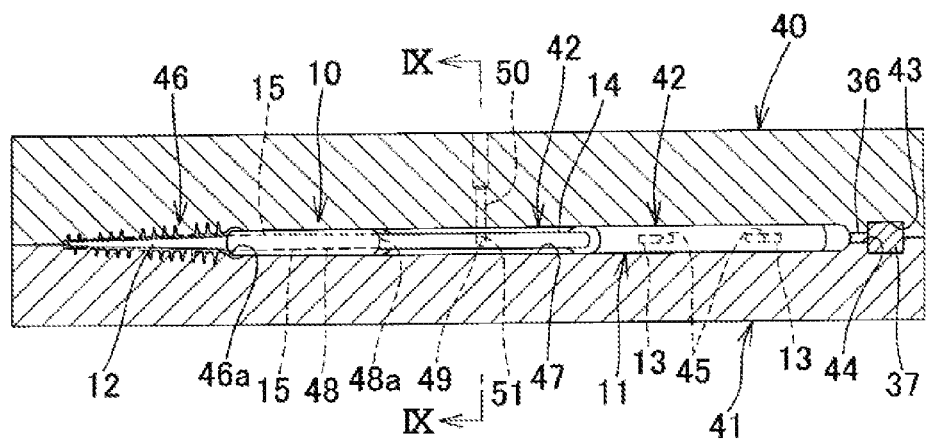
FIG. 8 is a longitudinal sectional view of the closed second molds with a primary molded product loaded therein, which is along the VIII-VIII line in FIG. 7(a).
Figure 9:
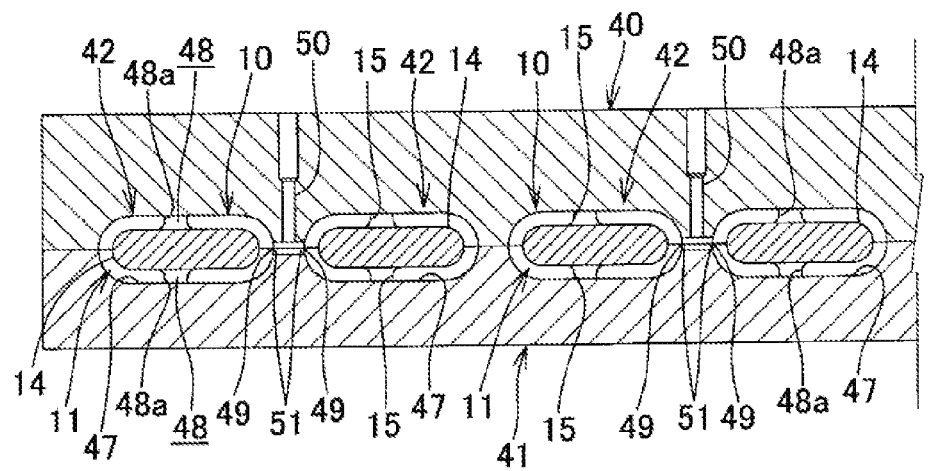
FIG. 9 is a sectional view along an IX-IX line of FIG. 8.

As illustrated in FIG. 7A, FIG. 7B, FIG. 8 and FIG. 9, the soft portion molding step includes placing, in the second molding space 42 of the second molds 40 and 41, the primary molded product 10A formed in the first molds 30 and 31; and then charging an elastomeric material into the second molding spaces 42 to form soft portions 20, so that as illustrated in FIGS. 5 and 6, an interdental cleaning device chain 5A is obtained, which includes a plurality of interdental cleaning devices 1 connected in parallel. Subsequently, the first runner portion 37, the first gate portions 36, supply route portions 52, and second gate portions 54 are removed, so that the interdental cleaning device chain 5 shown in FIG. 1 is obtained.

First, the second molds 40 and 41 used in the soft portion molding step will be described. The second molds 40 and 41 have a plurality of second molding spaces 42, which are formed at positions corresponding to those of the base portions 10 of the primary molded product 10A formed in the molds 30 and 31. The second molds 40 and 41 also have insertion spaces 43, 44 and 45 formed to accommodate the first runner portion 37, the first gate portions 36, and the connecting protrusions 13 of the primary molded product 10A.

The second molding spaces 42 formed between the second molds 40 and 41 and the base portions 10 each include a cleaning soft portion molding space 46 for surrounding the core portion 12; a non-slip portion molding space 47 for surrounding a middle portion of the handle portion 11; and a pair of connecting portion molding spaces 48 that allows the non-slip portion molding space 47 and the cleaning soft portion molding space 46 to communicate with each other.

A plurality of second molding spaces 42 are formed in parallel at the mating surfaces of the second molds 40 and 41. Second gates 49 for supplying an elastomeric material to the second molding spaces 42 each have an opening at a position substantially equally distant from the positions of two communicating openings 48a that are portions of the non-slip portion molding space 47 for molding the non-slip portion 22 and communicate with the connecting portion molding spaces 48 for molding the connecting portions 23. The second gates 49 may be formed at any positions of the second molds 40 and 41. Preferably, the second gates 49 are placed at the mating surfaces of the second molds 40 and 41 so that the second molds 40 and 41 can have a simple structure. Specifically, when the handle portions 11 are formed in a flat rod shape, the connecting portion molding spaces 48 may be placed at positions facing both wide surfaces of the handle portion 11, and the opening of the second gate 49 may be placed at a position facing the narrow side of the non-slip portion molding space 47. The two communicating openings 48a of the connecting portion molding spaces 48 may be formed at any positions as long as they are equally distant from the second gate 49. Preferably, the communicating openings 48a are formed at two sites symmetrically apart by 180 degrees in the circumferential direction about the central axis of the cleaning soft portion molding space 46 for molding the cleaning soft portion 21. When the second gates 49 are formed at the mating surfaces of the second molds 40 and 41, they may be each located at a position facing the widthwise center of both wide surfaces of the handle portions 11. The second gates 49 preferably have a diameter of 0.1 mm or more and 1.0 mm or less. The second gates 49 have a circular shape. It will be understood that this is not intended to limit the present invention and the second gates 49 may have any other shape.

Both connecting portion molding spaces 48 are formed to extend substantially parallel to each other from the communicating openings 48a to the front end side of the second molding space 42. The front ends of both connecting portion molding spaces 48 are formed to connect and communicate with two portions of an insertion limiting portion molding space 46a at the base end of the cleaning soft portion molding space 46.

In the second mold 40, common supply channels 50 each for supplying an elastomeric material to both of adjacent non-slip portion molding spaces 47, which define a pair of adjacent second molding spaces 42, are each formed to extend to the substantially central position between the adjacent non-slip portion molding spaces 47. In the second mold 40, individual supply channels 51 are also branched from the substantially central position to the opposed positions of the respective non-slip portion molding spaces 47 and formed to reach the second gates 49 opened to the non-slip portion molding spaces 47. The second mold 40 is so configured that an elastomeric material can be charged into each second molding space 42 through the common supply channel 50 and the individual supply channel 51 so that the soft portions 20 can be simultaneously molded on the base portions 10. As mentioned above, when the two communicating openings 48a are equally distant from the second gate 49, the elastomeric material can be supplied at the same timing to the two communicating openings 48a. Therefore, as illustrated in FIG. 10, the second molds 40 and 41 may have an individual supply channel 51 provided with a single unbranched supply channel 50A, instead of the supply channels 50 and 51, and the supply channel 50A may be formed to communicate with the second gate 49 at a middle portion in the thickness direction of the non-slip portion molding space 47 of each second molding space 42. Alternatively, as illustrated in FIG. 11(a), an interdental cleaning device 1E may have a handle portion 11E with a C-shaped concave portion 14E formed at the middle position, instead of the handle portion 11 and the loop-shaped concave portion 14, and may have a C-shaped non-slip portion 22E instead of the non-slip portion 22. Alternatively, as illustrated in FIG. 11(b), an interdental cleaning device 1F may have a handle portion 11F with a U-shaped concave portion 14F formed at the middle position, instead of the handle portion 11 and the loop-shaped concave portion 14, and may have a U-shaped non-slip portion 22F instead of the non-slip portion 22. Alternatively, as illustrated in FIG. 11(c), an interdental cleaning device 1G may have a handle portion 11G with a circular cross-section, instead of the handle portion 11, in which the handle portion 11G may have a circular ring-shaped concave portion 14G at the middle position, instead of the loop-shaped concave portion 14, and may have a circular ring-shaped non-slip portion 22G instead of the non-slip portion 22. Also in these cases, the second gate 49 may be formed at the corresponding position indicated by the arrow A in the second molds 40 and 41, so that the elastomeric material can be supplied at the same timing to the two communicating openings 48a formed at the base end of the connecting portions 23.

The second molds 40 and 41 may also have a plurality of holding pins capable of holding the core portions 12. The holding pins may be provided insertable into the cleaning soft portion molding spaces 46 so that each core portion 12 can be precisely aligned and held at the center of each cleaning soft portion molding space 46.

In the soft portion molding step, the primary molded product 10A having the handle portions 11 connected in parallel with the first runner portion 37 is placed in the second molds 40 and 41 in such a manner that the handle portions 11 are loaded into the second molding spaces 42, respectively, while both second molds 40 and 41 are closed. Subsequently, an elastomeric material is supplied to a second runner (not shown), so that the elastomeric material is supplied sequentially to the common supply channels 50, which are connected to the second runner, and supplied simultaneously to the pair of adjacent non-slip portion molding spaces 47 through the common supply channel 50, the individual supply channels 51, and the second gates 49, so that the elastomeric material is charged into the second molding spaces 42. In this process, when supplied to the non-slip portion molding space 47, the elastomeric material is charged into the non-slip portion molding space 47 and reaches, substantially at the same timing, a pair of communicating openings 48a equally distant from the second gate 49. The elastomeric material is then supplied from the pair of communicating openings 48a through the connecting portion molding spaces 48 to the insertion limiting portion molding space 46a with a loop shape at the base end of the cleaning soft portion molding space 46. The elastomeric material is retained transiently in the insertion limiting portion molding space 46a and then supplied from the insertion limiting portion molding space 46a to the front ends of the cleaning soft portion molding space 46 at substantially uniform timing over the entire circumference. Thus, the elastomeric material is charged into the cleaning soft portion molding space 46 until the front ends are filled with the elastomeric material.

After the elastomeric material is charged into the second molding spaces 42 in this way, the second molds 40 and 41 are opened, so that the interdental cleaning device chain 5A with the structure shown in FIGS. 5 and 6 is obtained. Subsequently, the first runner portion 37 and the first gate portions 36, which are made of the synthetic resin, are removed from the interdental cleaning device chain 5A, and supply channel portions 52 and second gate portions 54, which are made of the elastomeric material molded in the supply channels 50 and 51 and the second gates 49, are removed, so that an interdental cleaning device chain 5 is obtained.

As described above, each second gate 49 in the second molds 40 and 41 has an opening at a position substantially equally distant from the positions of the two communicating openings 48a that are portions of the non-slip portion molding space 47 for molding the non-slip portion 22 and communicate with the connecting portion molding spaces 48 for molding the connecting portions 23. In the soft portion molding step, the elastomeric material is charged from the second gate 49 into each second molding space 42 for the soft portion 20. Therefore, when supplied from the second gate 49 to the non-slip portion molding space 47, the elastomeric material can be supplied simultaneously to the connecting portion molding spaces 48 from the non-slip portion molding space 47. Therefore, the elastomeric material can be supplied to the cleaning soft portion molding space 46 at the same timing from the connecting portion molding spaces 48, which makes it possible to effectively prevent poor molding of the cleaning soft portion 21 and to improve the quality of the interdental cleaning device 1. In addition, the elastomeric material is charged from the base side of the core portion 12, which makes it possible to smoothly mold the non-slip portion 22 on the handle portion 11. In addition, the elastomeric material is charged from the base side of the core portion 12 with a large cross-section, which makes it possible to prevent the core portion 12 from being deformed by heat during the charging of the elastomeric material and to allow the front end portion of the core portion 12 to have a small diameter, so that the length of the cleaning portion 2 insertable between teeth can be made as large as possible to increase the ability to clean the space between teeth. In addition, the interdental cleaning device 1 manufactured by this method has the non-slip portion 22 and the connecting portions 23, which are formed of the elastomeric material on the handle portion 11. The non-slip portion 22 and the connecting portions 23 allow the interdental cleaning device 1 to have improved handleability.

Figure 13:
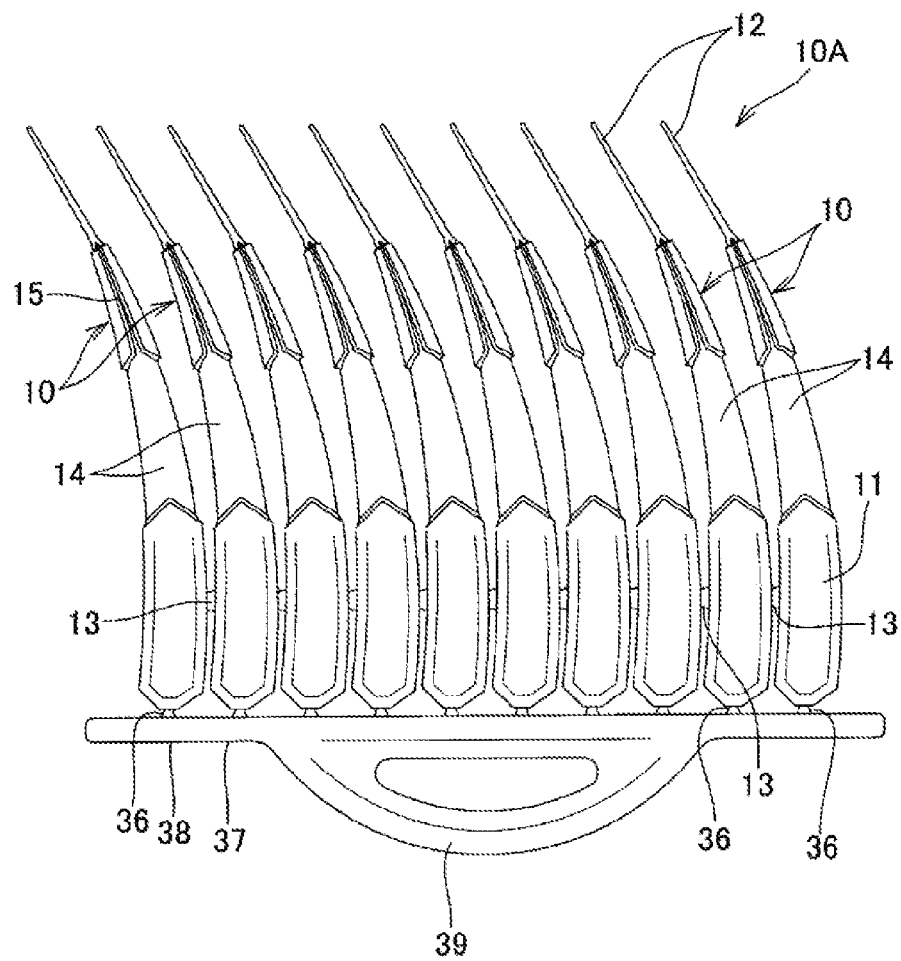
FIG. 13 is a front view illustrating a modified example of a primary molded product having base portions connected to one another.
Figure 14:
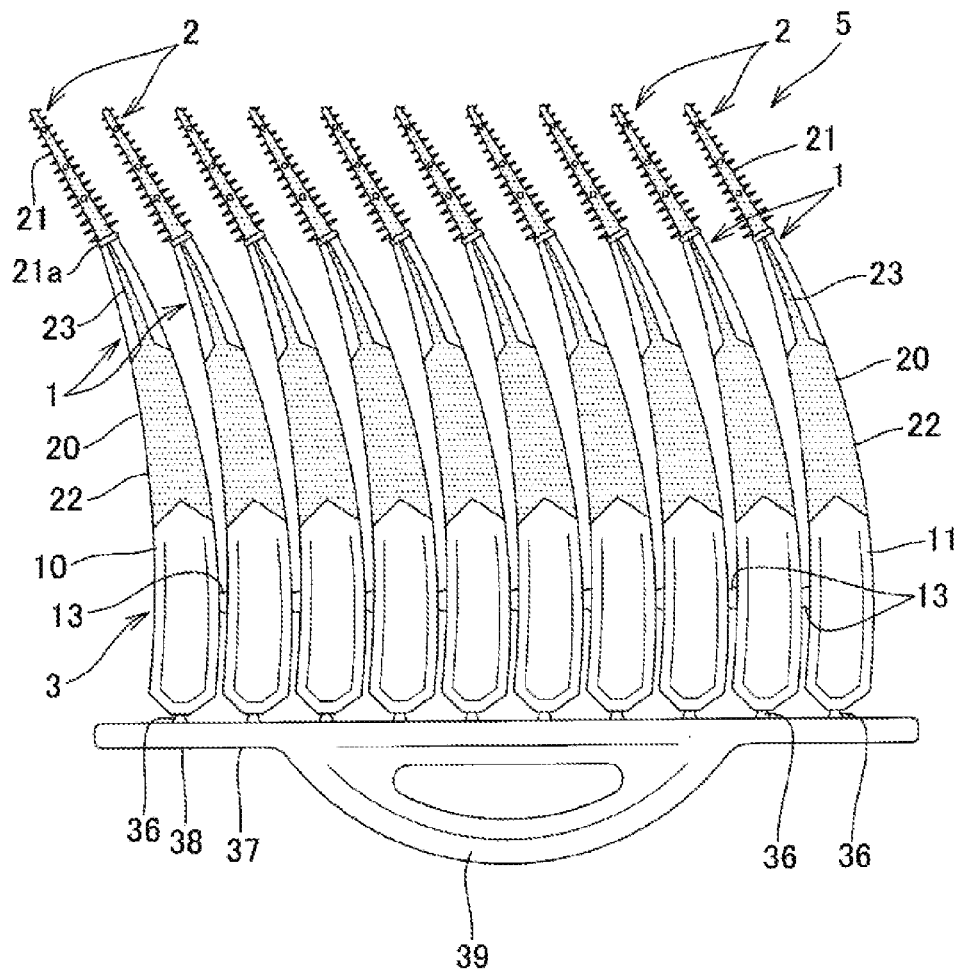
FIG. 14 is a front view illustrating a modified example of an interdental cleaning device chain.

Next, a modified example of the interdental cleaning device chain according to the present invention will be described with reference to FIGS. 13 and 14. In this modified example, the base portions 10 are connected to each other with only one connecting protrusion 13, and the first runner portion 37 and the first gate portions 36 are left unremoved when the interdental cleaning device chain 5 is completed.

In this structure, adjacent interdental cleaning devices 1 are connected to each other with one connecting protrusion 13, and each interdental cleaning device 1 is connected to the first runner portion 37 through the first gate portion 36, so that all the interdental cleaning devices 1 are connected through the first runner portion 37. Therefore, a sufficient level of connection strength can be secured between adjacent base portions 10, and even with only one connecting protrusion 13, the rupture or deformation of the base portions 10 can be prevented, which would otherwise also occur if the base portions 10 move relative to each other during the opening of the molds. In addition, the base portions 10 can be loaded at proper positions in the second molding spaces, so that good molding can be maintained. In addition, the user can easily separate the interdental cleaning device 1 to be used by first pulling the interdental cleaning device 1 to break the connecting protrusion 13 while holding the first runner portion 37 and then pulling it as-is to break the first gate portion 36. This makes the interdental cleaning device 1 convenient for use.

The first runner portion 37, which is left as part of the product (the interdental cleaning device chain 5) as mentioned above, may have various shapes. In this example, a gripping portion 39 for allowing the user to grip it is provided to protrude from the opposite side of the first runner portion 37 from the interdental cleaning device 1 side from which the first gate portions 36, which are also left as part of the product, protrude. Therefore, the product is configured to be easily held by the user during use. More specifically, the first runner portion 37 includes a rod-shaped main body 38 extending in the direction where the interdental cleaning devices 1 are arranged; and a substantially C-shaped gripping portion 39 that curves from a position distant by about ¼ of the length of the rod-shaped main body 38 from its one end, extends to the side opposite to the interdental cleaning device 1 side, and returns to a position distant by about ¾ of the length from the one end. According to this configuration, the molding resin for the primary molded product can be supplied in a well-balanced manner to the respective molding spaces when injected from, for example, the central position of the gripping portion 39, which makes it possible to improve the quality of the primary molded product.

Next, another modified example of the interdental cleaning device chain according to the present invention will be described with reference to FIGS. 15(*a*) and 15(*b*). In this modified example, a region having through or bottomed holes 16 is provided at a base end side of each handle portion 11 rather than the non-slip portion 22-covered region of each handle portion 11, in other words, rather than the region of the loop-shaped concave portion 14 in this example. Such holes 16 will function as effective alignment portions for stable loading of the base portions at proper positions in the molding spaces, when the base portions 10 of the primary molded product 10A are placed in the second molding spaces and then the soft portions 20 are molded thereon. Such holes 16 can also reduce the amount of the synthetic resin material for the base portions 10, so that material cost and weight can be reduced. In addition, the presence of such holes 16 on the gripping portion base end side of the completed interdental cleaning device makes it possible to improve gripability and increase design variety. In this example, two through holes 16A are provided in each base portion 10, and a bottomed hole 16B is provided on each of the front and back sides between these holes 16A. The number, shape, and other features of the holes 16 are not limited to those at all.

While the embodiments of the present invention have been described above, it will be understood that the above embodiments are not intended at all to limit the present invention and the features of the embodiments may be changed or modified without departing from the gist of the present invention. For example, while the embodiments show cases where two types of molds (first and second molds) are used for molding, the present invention also encompasses embodiments in which molding is performed in one movable mold, which can be rotated.

REFERENCE SIGNS LIST

1 Interdental cleaning device
2 Cleaning portion
3 Gripping portion
5 Interdental cleaning device chain
5A Interdental cleaning device chain
10 Base portion
10A Primary molded product
11 Handle portion
12 Core portion
13 Connecting protrusion
14 Loop-shaped concave portion
15 Groove
16 (16A, 16B) Hole
20 Soft portion
21 Cleaning soft portion
21*a* Insertion limiting portion
21*b* Cover portion
21*c* Protrusion
22 Non-slip portion
23 Connecting portion
1A Interdental cleaning device
11A Handle portion
1B Interdental cleaning device
11B Handle portion
1C Interdental cleaning device
11C Handle portion
1D Interdental cleaning device
11D Handle portion
1E Interdental cleaning device
11E Handle portion
14E C-shaped concave portion
22E Non-slip portion
1F Interdental cleaning device
11F Handle portion
14F U-shaped concave portion
22F Non-slip portion
1G Interdental cleaning device
11G Handle portion
14G Circular ring-shaped concave portion
22G Non-slip portion
30 First mold
31 First mold
32 First molding space
32*a* Core portion molding portion
32*b* Handle portion molding portion
33 First runner
34 First gate
35 Connecting protrusion molding portion
36 First gate portion
37 First runner portion
38 Rod-shaped main body
39 Gripping portion
40 Second mold
41 Second mold
42 Second molding space
43 Insertion space
44 Insertion space
45 Insertion space
46 Cleaning soft portion molding space
46*a* Insertion limiting portion molding space
47 Non-slip portion molding space
48 Connecting portion molding space
48*a* Communicating opening
49 Second gate
50 Common supply channel
51 Individual supply channel
52 Supply channel portion
54 Second gate portion
50A Supply channel
211 Front end of protrusion
212 Rear end of base end portion of protrusion

The invention claimed is:

1. A method for manufacturing an interdental cleaning device including:
a base portion that is formed by molding a synthetic resin material and includes a handle portion and a core portion provided at a front end of the handle portion and having a slender shaft shape; and
a soft portion that is formed on the base portion by molding an elastomeric material, and includes a cleaning soft portion substantially covering at least part of the core portion, a non-slip portion substantially covering at least part of the handle portion, and connecting portions also covering at least part of the handle portion, extending from two sites of the non-slip portion, and being connected to the cleaning soft portion, the method comprising:
forming, in the base portion, a concave portion so as to correspond to the non-slip portion, and a groove so as to correspond to each of the connecting portions;
providing, in a mold, a plurality of molding spaces in parallel for molding soft portions including the soft portion;
providing a gate of a mold, which opens to each of the plurality of molding spaces, to open at a mating surface of the mold, and open at a position substantially equally distant from positions of two communicating openings of a non-slip molding space for molding the non-slip portion, the two communicating openings communicating with connecting portion molding spaces for molding the connecting portions; and
charging the elastomeric material from the gate into a soft portion molding space to fill the soft portion molding space.

2. The method according to claim 1, wherein the connecting portion molding spaces are located to connect and communicate with two sites that are substantially symmetrically apart by substantially 180 degrees in a circumferential direction about a central axis of a cleaning soft portion molding space for molding the cleaning soft portion.

3. The method according to claim 1, wherein
the mold has a cleaning soft portion base end portion molding space that is for molding a loop-shaped cleaning soft portion base end portion and is located at a base end of the cleaning soft portion molding space, and
the connecting portion molding spaces are located to connect and communicate with two sites of the cleaning soft portion base end portion molding space.

4. The method according to claim 1, wherein
the handle portion is formed in a substantially flat rod shape,
the connecting portion molding spaces are placed at positions facing both wide surfaces of the handle portion, and
the opening of the gate is placed at a position facing a narrow surface of the handle portion.

5. The method according to claim 1, wherein
the mold has a plurality of molding spaces arranged in parallel each for molding the soft portion,
the mold has a common supply channel for supplying the elastomeric material to both of adjacent non-slip portion molding spaces, which constitute a pair of two of the molding spaces arranged in parallel, the common supply channel extending to a substantially central position between the adjacent non-slip portion molding spaces,
the mold has individual supply channels that are branched from the substantially central position and formed to reach openings of the gates formed at opposed positions of the respective non-slip portion molding spaces, and
the elastomeric material is charged into each of the molding spaces through the common supply channel and the individual supply channels so that soft portions including the soft portion are simultaneously molded on a plurality of base portions including the base portion.

6. The method according to claim 1, wherein a region having a through or bottomed hole is provided on the handle portion in a range from a base end side to a non-slip portion-covered region.

* * * * *